United States Patent [19]

Henry

[11] Patent Number: 5,052,389

[45] Date of Patent: Oct. 1, 1991

[54] LOW-POWER A/D CONVERTER FOR AN IMPLANTABLE MEDICAL DEVICE AND METHOD OF USE

[75] Inventor: Donald A. Henry, Greensburg, Pa.

[73] Assignee: Cook Pacemaker Corporation, Leechburg, Pa.

[21] Appl. No.: 558,616

[22] Filed: Jul. 26, 1990

[51] Int. Cl.$^5$ .............................................. A61N 1/36
[52] U.S. Cl. .............................................. 128/419 PG
[58] Field of Search ........... 128/419 C, 419 D, 419 E, 128/419 F, 419 G, 419 PG, 419 PT, 903, 904; 604/65-67

[56] References Cited

U.S. PATENT DOCUMENTS

| | | | |
|---|---|---|---|
| 4,023,121 | 5/1977 | Alley | 128/419 PG |
| 4,026,305 | 5/1977 | Brownlee et al. | 128/419 PT |
| 4,164,944 | 8/1979 | Alley et al. | 128/419 PG |
| 4,281,664 | 8/1981 | Duggan | 128/696 |
| 4,404,972 | 9/1983 | Gordon et al. | 128/419 PG |
| 4,409,984 | 10/1983 | Dick | 128/696 |
| 4,467,807 | 8/1984 | Bornzin | 128/419 PG |
| 4,543,953 | 10/1985 | Slocum et al. | 128/419 PT |
| 4,543,954 | 10/1985 | Cook et al. | 128/419 PG |
| 4,592,360 | 6/1986 | Lesnick | 128/419 PG |
| 4,741,340 | 5/1988 | Batina et al. | 128/419 PT |
| 4,757,816 | 7/1988 | Ryan et al. | 128/419 PT |
| 4,779,617 | 10/1988 | Whigham | 129/419 P |
| 4,791,936 | 12/1988 | Snell et al. | 128/697 |

FOREIGN PATENT DOCUMENTS 2492262 10/1980 France .
2026870A 2/1980 United Kingdom .

Primary Examiner—William E. Kamm
Attorney, Agent, or Firm—Woodard, Emhardt, Naughton, Moriarty & McNett

[57] ABSTRACT

A low-power A/D converter for an implantable medical device. The converter includes a high-frequency oscillator capable of generating clock pulses at a frequency substantially higher than the main clock frequency of the implantable device, and an oscillator-gating circuit for enabling the oscillator for a voltage-dependent variable time interval. The gating circuit includes a voltage-controlled monostable multivibrator for generating a gate control pulse having a pulse width corresponding to the value of an analog signal representative of a physiological parameter sensed by the implantable device. A timing controller, which operates at a low frequency under control of a crystal-controlled clock, supplies a trigger pulse to the voltage-controlled monostable at a predetermined first point in the variable time interval and generates an enable pulse at a predetermined second point in the variable time interval. In response to the enable pulse, the A/D converter enables the oscillator at the second point and, in response to the gate control pulse, disables the oscillator at the end of the variable time interval. A counter coupled to the oscillator counts the clock pulses generated between the second point and the end of the variable time interval.

7 Claims, 6 Drawing Sheets

LOW-POWER A/D CONVERTER FOR AN IMPLANTABLE MEDICAL DEVICE AND METHOD OF USE

BACKGROUND OF THE INVENTION

This invention relates to analog-to-digital (A/D) converters for use in pacemakers and other implantable medical devices, and more particularly to systems and methods for low-power A/D conversion for use in such devices.

Historically, the processing of analog signals within electronic devices such as implantable cardiac pacemakers has been performed by using conventional analog techniques, employing active components (transistors in one form or another) operating in a linear mode along with associated passive components controlling the overall circuit characteristics (gain, bandpass, etc.). Even though there has long been circuitry which could convert analog signals into digital form, A/D converters have until very recently been considered impractical for use in implantable devices.

One of the prime considerations for the pacemaker circuit designer is circuit current consumption. To achieve maximum device life, all circuitry must consume minimal current from the internal power cell. Typically, A/D converter circuits consume excessive amounts of current for use in this application.

In recent years, ultra-low-power digital microprocessors have become available and their use in cardiac pacemakers is becoming commonplace. Because of this, the processing and storage capabilities of pacemakers have been significantly enhanced, such that "software" control of analog input signal processing, including processing of the intracardiac ECG, has become a real possibility, along with development of algorithms for recognizing and detecting specific cardiac arrhythmias. It has been known since the advent of exercise-responsive pacemakers at least a decade ago that practical implementation of algorithms responsive to physiological parameters indicative of exercise would virtually require digital processing, and that such processing would require not only low-power digital logic devices, but also a low-power A/D converter. The inadequacy of available A/D converters was and continues to be compounded by other electrical and physical constraints imposed on pacemakers and other implantable devices, including the need for low-voltage operation, minimum circuit parts count, circuit reproducibility, compatibility with active devices available for such applications, acceptable analog bandwidths, minimum "active trims", and high finished-circuit yields.

Various attempts have been made to solve one or more of these problems, and various types of A/D converters have been proposed for use in pacemakers or other implantable devices, as exemplified by the following U.S. and foreign patent references:

| U.S. Pat. No. | Inventor | Issue Date |
| --- | --- | --- |
| 4,409,984 | Dick | Oct. 18, 1983 |
| 4,467,807 | Bornzin | Aug. 28, 1984 |
| 4,543,953 | Slocum et al. | Oct. 1, 1985 |
| 4,543,954 | Cook et al. | Oct. 1, 1985 |
| 4,757,816 | Ryan et al. | Jul. 9, 1988 |
| Foreign Patent Document | Applicant | Published |
| GB 2,026,870A | Medtronic | Feb. 13, 1980 |

An early proposal for a low-power A/D converter for a pacemaker is described in the above-referenced UK patent application No. GB 2,026,870A of Medtronic, particularly FIGS. 8 and 10 therein. In the disclosed device, an analog voltage to be converted to digital form is applied to the input of a voltage-controlled oscillator (VCO) whose output is applied to the input of a counter which counts up for a fixed period of time. The VCO input is then switched over to a reference voltage and the counter is placed in downcount mode. A second counter counts clock pulses from a second clock source until the first counter counts down to zero, such that the count in the second counter is directly proportional to the unknown input voltage. The second clock source is said to impose a minimal drain upon the pacer battery. The VCO is turned off during a wait mode for the A/D converter to conserve power. The converter rests in wait mode, with the last converted digital word resting in the second counter, until it receives a strobe pulse. Although the VCO duty cycle is controlled to reduce A/D converter power consumption, the VCO is on during the entire digitizing process, i.e., the up-count and down-count cycles of its associated counter, for each sample. The application indicates that various analog values can be converted to digital form, such as power supply voltage and the P and R waves of the patient's EKG.

The above-referenced patent references also provide evidence of various problems associated with A/D conversion in pacemakers. For example, Dick points out that A/D converters are rather costly, and proposes instead a technique of analog-to-FM-to-digital-to-analog conversion without using an A/D converter, to obtain a digital representation of an analog signal such as an ECG signal or other analog physiological parameter originating in a patient. The technique includes counting high-rate clock pulses during four FM periods to produce a count that is proportional to the time per FM period, and then calculating the reciprocal of time to produce a digital number that is proportional to frequency and, hence, to the instantaneous amplitude of the analog input voltage.

A/D converters were also avoided by Slocum et al. in U.S. Pat. No. 4,543,953, in which the stated general object of the invention was to transmit a reliable high-fidelity analog signal from the implant without excessive power consumption. Slocum et al. recognized the desirability of the intracardiac electrogram (ICEG) signal as well as the extreme difficulty in reliably transmitting the ICEG signal given the battery power constraints of the pacer. Slocum et al. further recognized that A/D conversion of the ICEG signal would be ideal given the proper sampling rate because of the inherent fidelity of the signal, but rejected the technique because A/D converters consume excessive power. The proposed alternative is an analog telemetry system.

A telemetry system is also proposed in the later issued patent to Ryan et al. as a simple technique of transmitting internal signals such as the intracardiac electrogram from an implanted pacer in a digital transmission rather than in an analog transmission, "but which also eliminates the usual steps needed in an analog-to-digital conversion system."

SUMMARY OF THE INVENTION

The present invention provides a low-power A/D converter for an implantable medical device, the converter having a high-frequency oscillator for generating clock pulses at a predetermined frequency substantially higher than the main clock frequency of the implantable device, an oscillator-gating circuit for enabling the high-frequency oscillator for a voltage-dependent variable time interval, the gating circuit including a voltage-controlled monostable for generating a gate-control pulse having a pulse width corresponding to the value of an analog signal representative of a physiological parameter sensed by the implantable medical device. A counter coupled to the oscillator counts clock pulses generated during the variable time interval to produce a digital output for the A/D converter.

A general object of the present invention is to provide an improved A/D converter for pacemakers and other implantable medical devices.

Another object is to better accommodate the various electrical and physical constraints imposed on implantable devices such as cardiac pacemakers, defibrillators, cardioverters, implantable drug-dispensing devices, and other implantable devices such as for therapy or sensing with the respect to the brain, spinal cord, muscles, bones, nerves or other body organs or tissue. As used herein, a pacemaker is meant to include devices for controlled stimulation of a natural heart as well as pacing and control units for other devices such as artificial hearts and ventricular assist devices.

Other objects and advantages of the present invention will become apparent upon reading the following detailed description of the preferred embodiment in conjunction with the accompanying drawings.

DESCRIPTION OF THE PREFERRED EMBODIMENT

Figure 1:
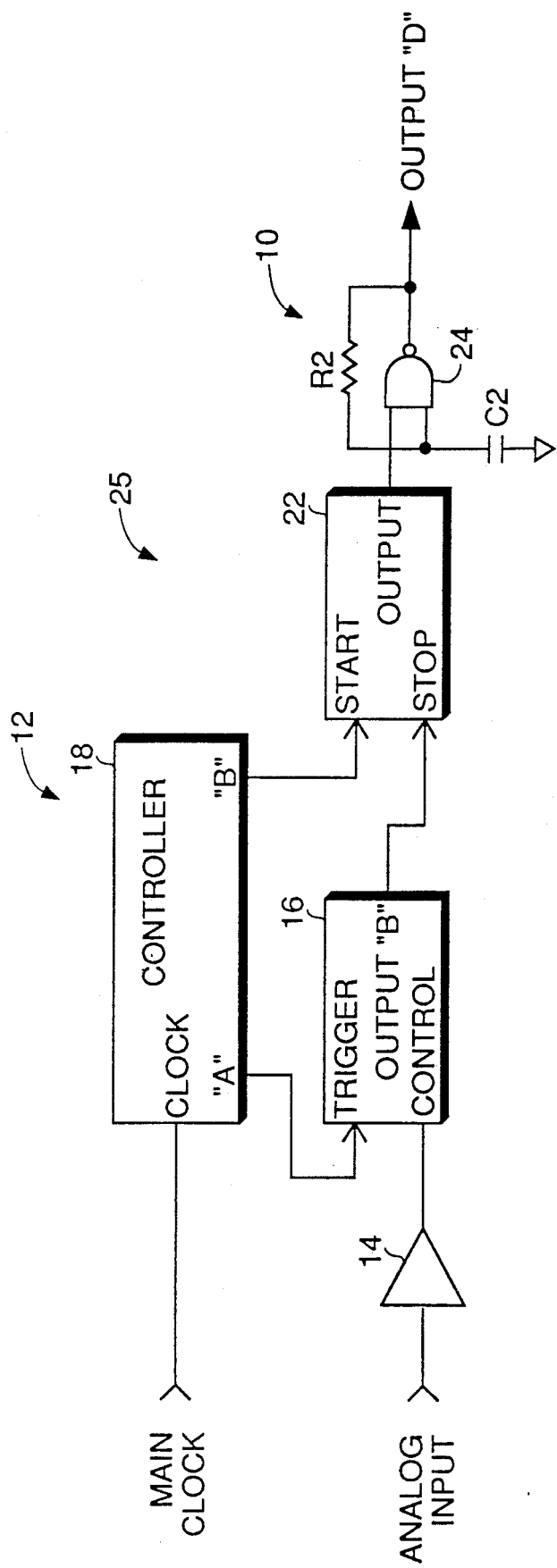
FIG. 1 is an illustration, partly in block diagram form and partly in schematic form, of the preferred embodiment of a high-frequency oscillator and oscillator-gating circuitry according to the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring to FIG. 1, a high-frequency oscillator 10 is selectively enabled and disabled by oscillator-gating circuitry denoted generally by reference numeral 12. In general terms, the gating circuitry gates the oscillator on, i.e., enables the oscillator to operate, for a variable time interval which is a function of the analog input to the converter. An analog input signal is first filtered and scaled in input amplifier 14 to produce a processed analog signal in a desired range as a control input for a voltage-controlled monostable (VCM) multivibrator 16. VCM 16 is further provided with a trigger input coupled to the "A" output of a controller 18 which generates control pulses under control of clock 20, which is a crystal-controlled low-frequency clock, preferably in the range of 20–50 kHz and most preferably 40 kHz. Power considerations dictate that the digital sections of pacemaker circuitry operate at relatively low frequencies such as those specified immediately above. An A/D converter according to the present invention may be contained within any one of the implantable medical devices previously described, but the preferred embodiment will be described in the context of a programmable pacemaker having a pulse generator and a microprocessor for monitoring and control of pacing functions. The pacemaker is powered by a battery in conventional fashion, and the battery also supplies power to the A/D converter.

Figure 2:
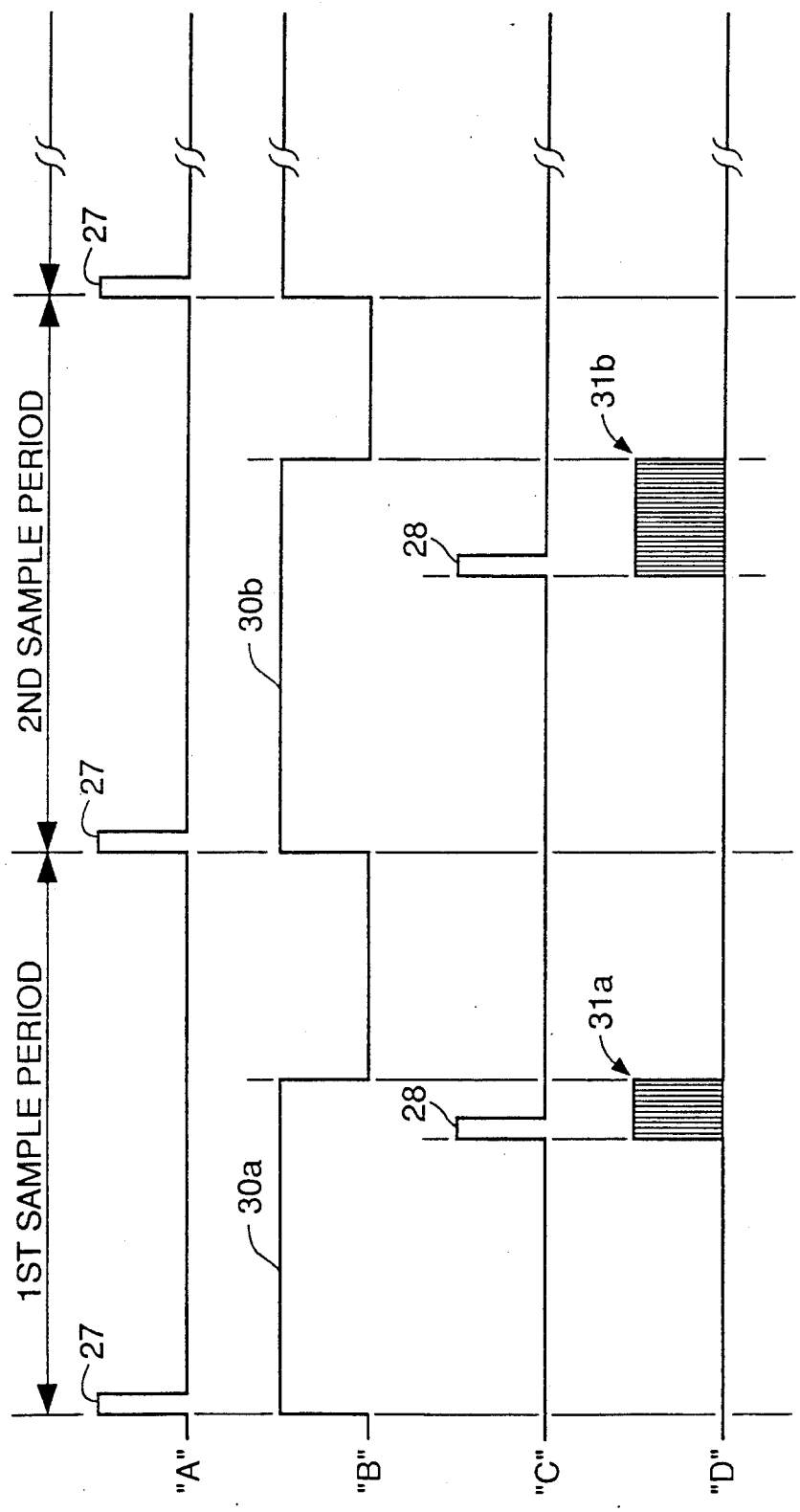
FIG. 2 is a timing diagram illustrating various waveforms generated by the circuit of FIG. 1.
Figure 3:
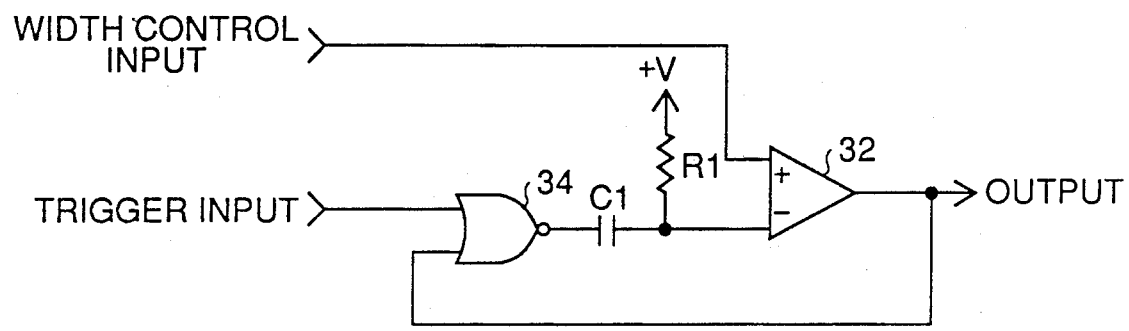
FIG. 3 is an electrical schematic of a voltage-controlled monostable (VCM) of the type depicted in block diagram form in FIG. 1.

Controller 18 includes counter circuitry enabling it to provide a trigger pulse "A" once every one millisecond (mS), which is the duration of each sample period in one embodiment of the present invention, and a gate control pulse "C" 600 microseconds ($\mu$S) after each trigger pulse "A", as illustrated in FIG. 2. VCM 16, configured as shown in FIG. 3, responds to each trigger pulse by producing an output pulse "B" of varying duration depending upon the instantaneous voltage of the analog input supply to the control input of VCM 16. As will be appreciated by those skilled in the art, the voltage-controlled monostable, or one-shot, is triggered by a high ("1") logic level on the trigger input, connected to one input of NOR gate 34, whereupon the output of comparator 32 goes high and remains high until capacitor C1 charges, through resistor R1, to a voltage exceeding the instantaneous voltage of the analog input signal which is supplied to the width control input. The value of R1 should be kept as high as possible so as to minimize current consumption. Presently preferred values of R1 and C1 are 8.2 M$\Omega$ and 220 pF, respectively.

The R1–C1 time constant of VCM 16 and the scaling components in input amplifier 14 are selected such that the duration of each output pulse of the monostable varies linearly in a $\pm$100-microsecond ($\mu$S) range as a function of analog input voltage for an input range of $\pm$20 millivolts (mV). The linear range preferably has a minimum time interval of 600 $\mu$S, corresponding to an input voltage of $-20$ mV, and a maximum time interval of 800 $\mu$S, corresponding to an input voltage of $+20$ mV. Thus, the pulse width of output pulses "B" varies as illustrated by pulses 70a and 70b in FIG. 3, with a maximum variation, or active linear range, of 200 $\mu$S. That is, the trailing edge of gate control pulse "B" occurs within 200 $\mu$S after the leading edge of enable pulse "C". Note that pulses 28 in FIG. 2 occur at the same time each sample period, with their leading edges occurring 600 μS after the leading edges of the respective trigger pulses 27.

Figure 4:
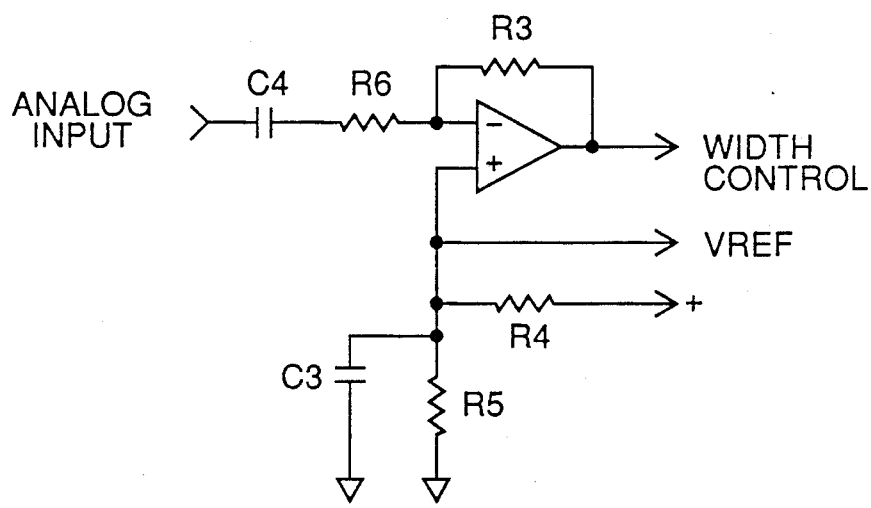
FIG. 4 is an electrical schematic of an analog input amplifier of the type shown in FIG. 1.

Input amplifier 14 is configured as shown in FIG. 4, and is preferably an op amp circuit using one of the two op amps in a 4575 dual/dual amplifier-comparator in the 4000 series of CMOS devices. One of the two comparators in the 4575 is preferably used for the comparator 32 in VCM 16. The presently preferred values for the passive components in input amplifier 14 are as follows:

| Component | Value |
|---|---|
| R6, R5 | 1 MΩ |
| R3 | 3.3 MΩ |
| R4 | 1.8 MΩ |
| C4 | 0.1 μF |
| C3 | 1 μF |

An enable/disable latch 22 is set to a high logic state in response to the leading edge of enable pulse "C" and is reset to a low logic state in response to the trailing edge of gate control pulse "B", thereby gating high-frequency oscillator 10 on for a time interval equal to that between the leading edge of pulse "C" and the trailing edge of pulse "B", which time interval corresponds to the value of the analog input signal in the manner described above. High-frequency oscillator 10 responds by generating an output "D" consisting of a pulse burst of varying duration, as illustrated by pulse bursts 31a and 31b in FIG. 2. Oscillator 10 is a relaxation oscillator configured with a resistor R2 and capacitor C2 connected around a two-input NAND gate 24 as shown in FIG. 1, one input of the NAND gate being connected to the output of latch 22 as an enable line. The passive components R2 and C2 are preferably selected such that the frequency of operation of the oscillator is 500 kHz, with the value of R2 kept as high as possible so as to minimize the charging and discharging current through C2. Presently preferred values for R2 and C2 are 20 KΩ and 22 pF, respectively.

The above-mentioned 1 kHz A/D sampling rate produces a resolution of 100 high-frequency oscillator clock cycles, or counts, for a VCM output pulse duration of 200 μS, and is adequate for processing the intracardiac ECG in some applications. Even greater resolution than that described above can be achieved by operating at a 500 Hz A/D sampling rate, which still provides adequate frequency response for intracardiac ECG processing. For this purpose, the A/D converter sample period is set to 2 mS in the preferred embodiment of the present invention, and the VCM is triggered twice every sample period. This effectively produces a 400-μS active VCM range which increases the resolution from approximately 6 bits to 7 bits (200 counts), as will be explained later.

Figure 5:
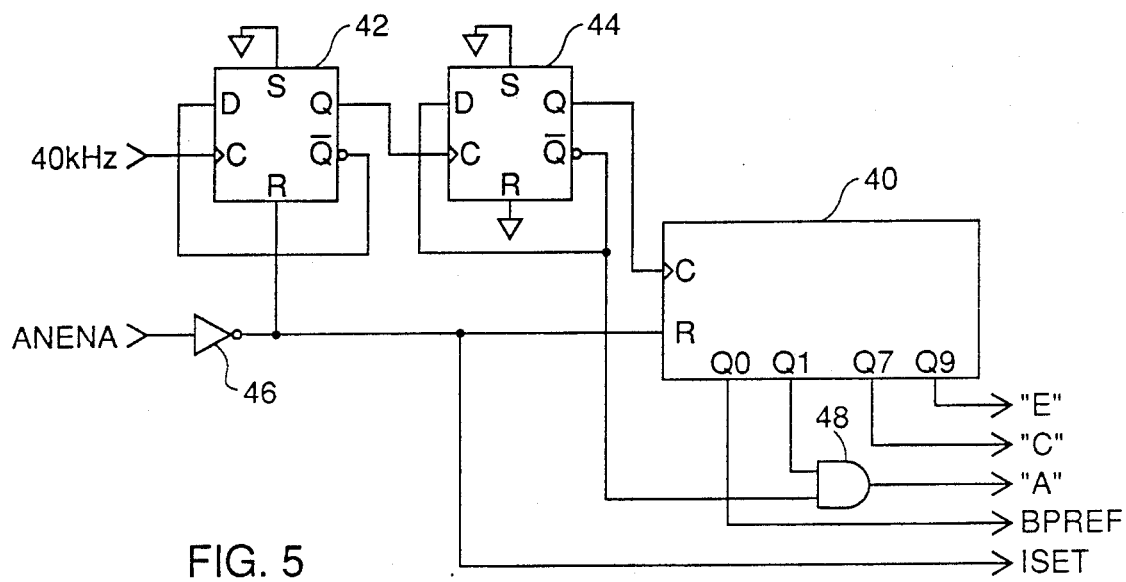
FIG. 5 is an electrical schematic of a controller of the type shown in FIG. 1.

Controller 18 is shown in further detail in FIG. 5, in which a counter 40 is driven by a 10 kHz clock derived from the 40 kHz main clock of the implantable device via a frequency divider consisting of a pair of D flip-flops 42 and 44 interconnected as shown in the drawing. Counter 40 is preferably a 4017 decade counter. The outputs of the counter sequentially go high for 100 μS each, whereby an "A" trigger pulse is generated once each millisecond and output "C" connected to the Q7 pin of counter 40 goes high 600 μS after each trigger pulse. Similarly, for reasons which will be explained, counter 40 generates an "E" pulse 800 μS after each "A" trigger pulse. In one embodiment the duration of output pulse "A" is limited to 50 μS by an AND gate 48 which receives the Q1 output pulse from counter 40 at one input and the complement of the 10 kHz clock signal at the other, whereby the AND gate output is high only during the second half of the 100 μS output pulse at the Q1 output. Alternatively, the "A" trigger pulses are taken directly from the Q1 output of counter 40 rather than through the gate shown in the drawing. In addition to the other pulses described above, counter 40 also generates a pulse at output Q0 100 μS before each "A" trigger pulse as a bit position reference (BPREF), for reasons which will be explained shortly. Controller 18 is held in a reset condition, through inverter 46, by a low logic state on the analog enable (ANENA) control line until A/D conversion is to be performed. The ANENA line is connected to the pacemaker microprocessor, and is switched to a high state under microprocessor control to enable A/D conversion. The microprocessor generates the appropriate control signals for the A/D converter in response to external command signals received via a communications coupling coil and processed through programming receiver circuitry (not shown) within the pacemaker.

The output of inverter 46 is also connected to the ISET inputs of the op amp in input amplifier 14 and the comparator in VCM 16 through current-setting resistors, preferably through an individual 10 MΩ resistor for each such ISET input, in order to reduce the drain on the pacemaker battery during operation. When A/D conversion is not desired, the drain on the battery can be minimized by disabling the op amp and comparator; this is accomplished by setting the ANENA control line low and thereby supplying a high output state at the output of inverter 46.

Figure 6:
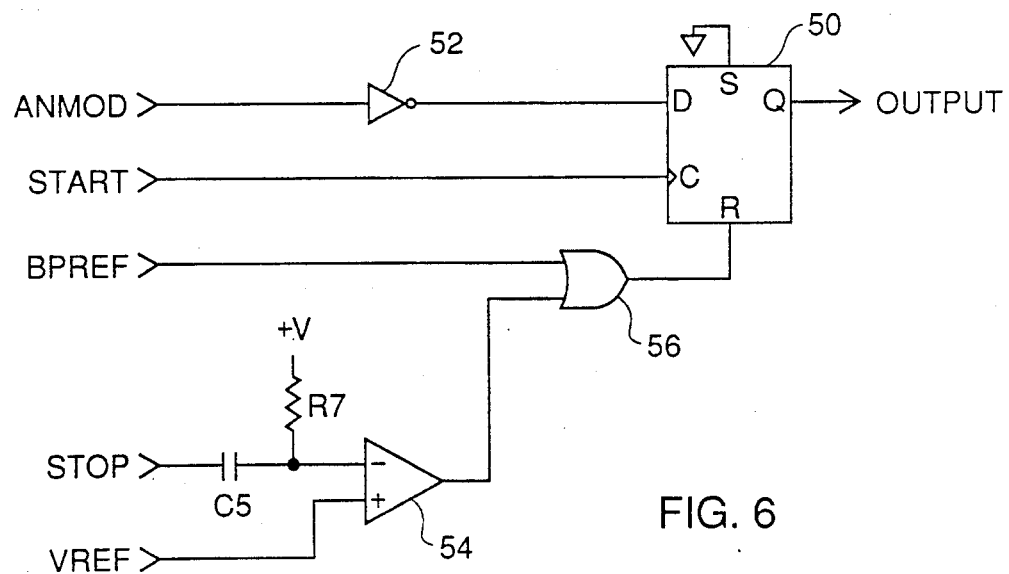
FIG. 6 is an electrical schematic of an oscillator-gating latch of the type shown in FIG. 1.

As shown in detail in FIG. 6, enable/disable latch 22 is designed around a D flip-flop 50 which receives its clock pulses on the START line connected to the "C" output of controller 18. The D input of flip-flop 50 is held high, through an inverter 52, by a low logic state on the analog mode (ANMOD) control line, connected to the microprocessor, when A/D conversion is performed, and is otherwise held low to disable operation of high-frequency oscillator 10. Flip-flop 50 is initialized by a reset pulse on the BPREF line which, through OR gate 56, resets the flip-flop if necessary at the beginning of operation of the A/D converter. Thereafter during A/D conversion, the flip-flop is cyclically clocked high and then reset by pulses appearing on the START and STOP lines, respectively. As will be appreciated by those skilled in the art, a one-shot formed by comparator 54 and associated passive components R7 and C5 is triggered by the trailing edge of a VCM output pulse "B" supplied to the STOP input; the output of comparator 54 goes high and remains high until capacitor C5 charges, through resistor R7, to a voltage exceeding the reference voltage VREF supplied to the non-inverting input of the comparator. The resulting output pulse from comparator 54 is coupled through OR gate 56 to the reset input of flip-flop 50, which switches low in response to the reset pulse and thereby disables the high-frequency oscillator. Comparator 54 is preferably one of the comparators in the above-referenced 4575 device, the operating current of which is controlled by the ISET line. Presently preferred values of R7 and C5 are 200 kΩ and 220 pF, respectively.

Figure 7:
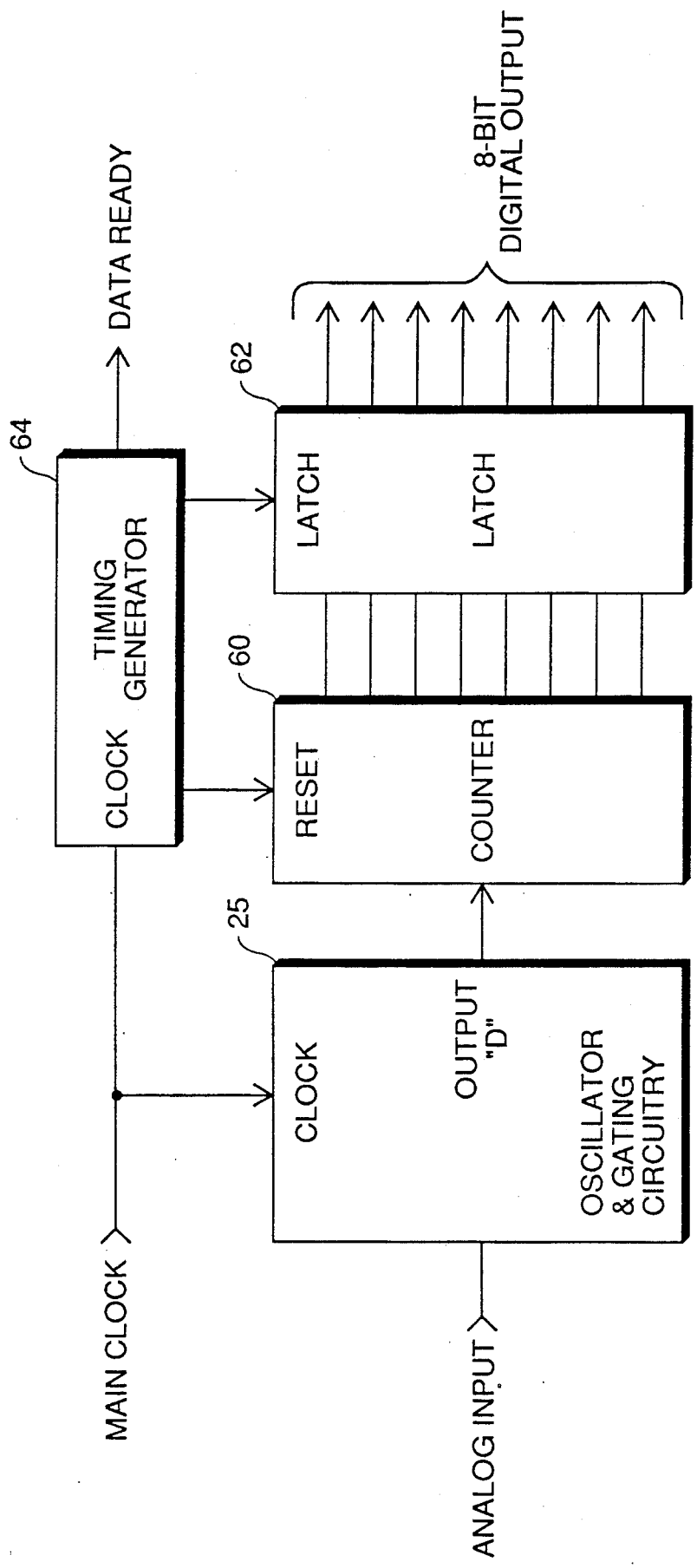
FIG. 7 is a block diagram of a complete A/D converter according to the preferred embodiment of the present invention.

Oscillator 10 and oscillator-gating circuitry 12 are depicted together in FIG. 7 as circuit block 25, output "D" of which is coupled to the clock input of an eight-bit counter 60 which in turn is coupled to an eight-bit latch 62 as illustrated in the drawing. The counter and latch operate under control of a timing generator 64 which, like oscillator and gating circuitry 25, receives its clock input from the main clock in the implantable device, and which generates reset and latch control pulses at appropriate times in each sample period, as will be explained shortly. In the embodiment of the A/D converter having a 1 kHz sampling rate, timing generator 64 sends a latch command to latch 62 after each pulse burst from oscillator 10, preferably prior to the leading edge of the next trigger pulse "A". Counter 60 is reset after its contents are latched into latch 62, by a reset pulse occurring, for example, at approximately the same time as the leading edge of the next trigger pulse "A". In the alternative embodiment having greater resolution as described above, the VCM is triggered twice per sample period of 2 mS, but the converter still latches the current output of the counter and resets the counter only once per sample period. The count of pulses from two successive pulse bursts in a given 2 mS sample period accumulates in counter 30, thereby enabling the counter to achieve a maximum output count of 200 for any given A/D sample.

In both embodiments, the digital output of latch 32 represents the digital value of a current analog input, the presence of which digital value is signalled by a DATA READY output pulse from timing generator 34. The digital output of latch 32 and the DATA READY signal from timing generator 34 are preferably coupled to the microprocessor in the pacemaker or other implantable device for internal processing or storage or for transmission via telemetry to some external device.

Figure 8:
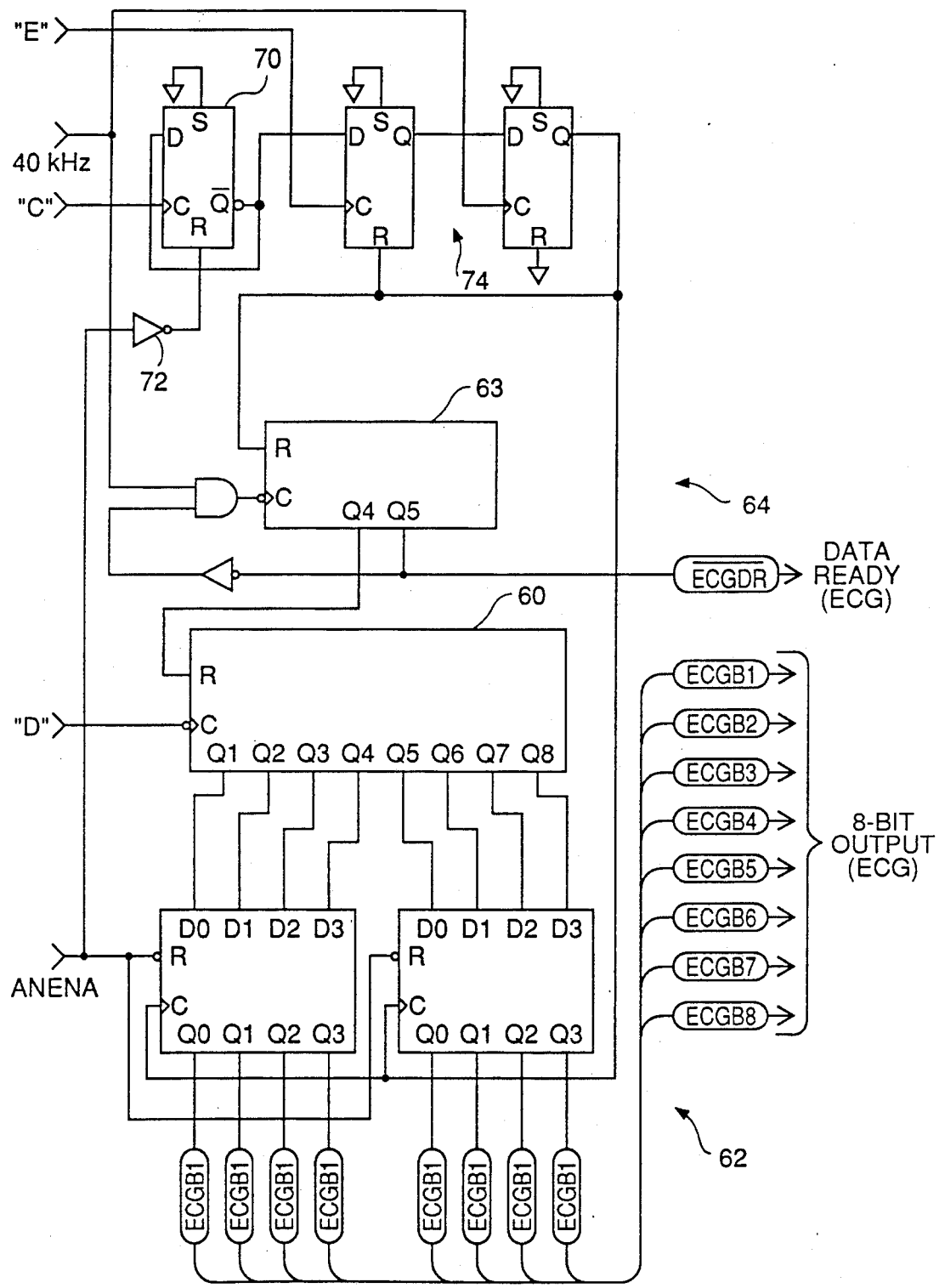
FIG. 8 is an electrical schematic of the counter, latch and timing generator circuitry shown in FIG. 7.

Referring now to FIG. 8, the electronic circuitry contained within the circuit blocks of FIG. 7 is shown in detail. Counter 60 is preferably a 4040 counter with its clock input connected to output "D" of the oscillator and gating circuitry. The data outputs of counter 60 are connected to the data inputs of two 4175 quad D flip-flops which together make up latch 62. The eight-bit output of latch 62 represents the output of the A/D converter, which provides an indication that the data is ready to be read by generating a high logic state on the DATA READY output line from the Q5 output of another counter 63, also preferably a 4040 counter, which, together with an associated AND gate and inverter connected as illustrated, forms a digital one-shot within timing generator 64. The timing generator also includes a D flip-flop 70 configured as a toggle flip-flop with its output connected to another digital one-shot 74 which uses a pair of D flip-flops connected as shown in the drawing.

In operation, the ANENA control line holds flip-flop 70 in a reset state through inverter 72, and similarly disables latch 62, until an A/D conversion is to be performed. Once the ANENA control line is set high to enable A/D conversion, counter 60, the outputs of which are all low at that time, begins to count pulses supplied from output "D" of high-frequency oscillator 10, which is gated on in response to the first pulse "C" generated after A/D conversion is enabled. This same "C" pulse which triggers latch 22 also triggers a chain of events in timing generator 64 that results in generation of a latch command, a reset pulse to counter 60, and a DATA READY output signal, in that order. More specifically, the $\overline{Q}$ output of flip-flop 70 is clocked low in response to the first pulse "C" generated after triggering of VCM 16 (FIG. 1) and thus the D input to one-shot 74 is switched low 200 $\mu$S before the expected arrival of the next clock pulse "E" which, as mentioned above, is generated 800 $\mu$S after each trigger pulse "A". As a result, one-shot 74 does not generate a latch command at the end of the first pulse burst from the high-frequency oscillator. However, flip-flop 70 toggles thereafter in response to pulses "C" and thereby enables one-shot 74 to generate a latch command following every second pulse burst. The pulse bursts last anywhere from 0–200 $\mu$S after oscillator 10 is gated on, i.e., until 600–800 $\mu$S after triggering of VCM 16, as explained above. At the first positive-going transition of the 40 kHz clock signal after the leading edge of the pulse "E", which is generated 800 $\mu$S after triggering of VCM 16, one-shot 74 goes high for 25 $\mu$S and thereby triggers latch 62 to latch the contents of counter 60. The output pulse from one-shot 74 also resets counter 63 within timing generator 64, in response to which the clock input of counter 63 is enabled and the counter begins counting 40 kHz clock pulses. 200 $\mu$S later, the Q4 output of counter 63 goes high and thereby clears counter 60, and the Q5 output of counter 63 goes high another 200 $\mu$S later, thereby disabling the clock input to counter 63 and maintaining a high logic state on the DATA READY line. This sequence is repeated for every A/D sample period, with counter 60 generating the cumulative count of the pulses in the two consecutive pulse bursts contained in each A/D sample period, and with such cumulative count being latched into latch 62 following the second pulse burst. Counter 60 is cleared at the end of each sample period.

If a 1 mS sample period is desired, flip-flop 70 may be eliminated and the D input of one-shot 74 may be tied high such that each pulse "E" causes latching of the counter contents corresponding to a single pulse burst. With the same operating frequency of the gated oscillator, the resolution and A/D conversion time would both be half that of the embodiment operating with a 2 mS sample period.

If desired, the A/D converter may also be provided with a multiplexed input. This is preferably done by providing a second input amplifier like amplifier 14 and a second VCM like VCM 16, and connecting the outputs of the two VCMs to an OR gate having its output connected to the STOP input of enable/disable latch 22. Channel selection logic would preferably steer trigger pulses "A" to a selected one of the two VCMs. Such an arrangement is described in my co-pending patent application Ser. No. 553,435 filed July 13, 1990 and entitled "Synchronous Telemetry System for an Implantable Medical Device," which patent application is hereby incorporated by reference.

All digital logic devices and other active components in the A/D converter disclosed herein are commercially available devices in the 4000 series of CMOS devices. CMOS logic inherently provides low power consumption, although it is relatively slow in comparison to other logic families. At a supply voltage of approximately 2 volts, as contemplated for the preferred embodiment of the present invention, the operating frequency of CMOS logic is limited to 1 MHz or less, and, as a design margin in the preferred embodiment, the operating frequency of high-frequency oscillator 10 is limited through the use of passive components to 500 kHz. Current consumption increases with operating frequency, such that relatively high amounts of current are consumed at frequencies, e.g., on the order of 100 kHz, which are substantially higher than frequencies of 50 kHz or less as conventionally used in the digital sections of pacemaker circuitry. Still greater amounts of current will be consumed during operation of high-frequency oscillator 10 at 500 kHz. However, by enabling the high-frequency oscillator only during the active linear portion of the VCM, the duty cycle is kept very low in the present invention and, consequently, current consumption is reduced significantly.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

I claim:

1. A low-power A/D converter for an implantable medical device operating with a main clock frequency, comprising:

high-frequency oscillator means for generating clock pulses at a predetermined frequency substantially higher than said main clock frequency;

oscillator gating means for enabling said oscillator means for a voltage-dependent variable time interval, said gating means including voltage-controlled monostable means for generating a gate control pulse having a pulse width corresponding to the value of an analog signal representative of a physiological parameter sensed by said implantable medical device; and counter means coupled to said oscillator means for counting clock pulses generated during said variable time interval.

2. The low-power A/D converter of claim 1, wherein said oscillator gating means includes means for enabling said oscillator means at a predetermined time after the beginning of said gate control pulse and disabling said oscillator means at the end of said gate control pulse.

3. The low-power A/D converter of claim 2, further comprising:

means for defining an A/D sample period for said A/D converter;

means for triggering said voltage-controlled monostable at least twice per sample period; and means for latching the current output of said counter means and resetting said counter means once per sample period.

4. A low-power A/D conversion method for an implantable medical device operating with a main clock frequency, comprising the steps:

providing an oscillator capable of generating clock pulses at a predetermined frequency substantially higher than said main clock frequency;

gating said oscillator on for a voltage-dependent variable time interval, said gating step including generating a gate control pulse having a pulse width corresponding to the value of an analog signal representative of a physiological parameter sensed by said implantable medical device; and counting clock pulses generated by said oscillator during said variable time interval.

5. The low-power A/D conversion method of claim 4, wherein said gating step includes enabling said oscillator at a predetermined time after the beginning of said gate control pulse and disabling said oscillator at the end of said gate control pulse.

6. The low-power A/D conversion method of claim 5, further comprising the steps:

defining an A/D sample period;

generating said gate control pulse at least twice per sample period; and latching the current count of said clock pulses and initializing said counting step once per sample period.

7. A low-power A/D converter for an implantable medical device operating with a main clock frequency, comprising:

high-frequency oscillator means for generating clock pulses at a predetermined frequency substantially higher than said main clock frequency;

oscillator gating means for enabling said oscillator means for a voltage-dependent variable time interval, said gating means including voltage-controlled monostable means for generating a gate control pulse having a pulse width corresponding to the value of an analog signal representative of a physiological parameter sensed by said implantable medical device;

a crystal-controlled low-frequency clock;

a timing controller having a clock input connected to said low-frequency clock, said timing controller including means for supplying a trigger pulse to said voltage-controlled monostable at a predetermined first point in said variable time interval and means for generating an enable pulse at a predetermined second point in said variable time interval;

means responsive to said enable pulse for enabling said oscillator means at said second point in said variable time interval;

means responsive to said gate control pulse for disabling said oscillator means at the end of said variable time interval; and counter means coupled to said oscillator means for counting clock pulses generated between said second point and the end of said variable time interval.

* * * * *